(12) United States Patent
Pacetti et al.

(10) Patent No.: US 8,573,148 B2
(45) Date of Patent: Nov. 5, 2013

(54) SYSTEM FOR COATING A STENT

(75) Inventors: Stephen D. Pacetti, San Jose, CA (US); Laura Melton Kalvass, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1010 days.

(21) Appl. No.: 12/554,671

(22) Filed: Sep. 4, 2009

(65) Prior Publication Data

US 2011/0059227 A1    Mar. 10, 2011

(51) Int. Cl.
  *B05C 13/00* (2006.01)
  *B05D 3/00* (2006.01)

(52) U.S. Cl.
  USPC ............................... 118/500; 427/2.1

(58) Field of Classification Search
  None
  See application file for complete search history.

(56) References Cited

U.S. PATENT DOCUMENTS

| | | | |
|---|---|---|---|
| 2,387,300 A * | 10/1945 | Ronei | 118/52 |
| 3,517,644 A * | 6/1970 | Baer | 118/716 |
| 4,325,320 A * | 4/1982 | Kirisawa | 118/52 |
| 5,458,917 A * | 10/1995 | Motohashi et al. | 427/240 |
| 6,368,658 B1 * | 4/2002 | Schwarz et al. | 427/2.15 |
| 6,572,644 B1 | 6/2003 | Moein | |
| 6,955,723 B2 | 10/2005 | Pacetti et al. | |
| 7,074,276 B1 | 7/2006 | Van Sciver et al. | |
| 7,416,609 B1 | 8/2008 | Madriaga et al. | |
| 2003/0157241 A1 * | 8/2003 | Hossainy et al. | 427/2.24 |
| 2004/0261698 A1 * | 12/2004 | Roorda et al. | 118/416 |
| 2005/0085889 A1 | 4/2005 | Sundar | |
| 2005/0106204 A1 | 5/2005 | Hossainy et al. | |
| 2006/0207501 A1 * | 9/2006 | Van Sciver et al. | 118/500 |
| 2007/0141232 A1 | 6/2007 | Tochterman et al. | |
| 2007/0163495 A1 * | 7/2007 | Kokish et al. | 118/500 |
| 2007/0259099 A1 * | 11/2007 | Van Sciver | 427/2.24 |
| 2008/0067728 A1 | 3/2008 | Plans et al. | |
| 2008/0213462 A1 | 9/2008 | Roorda et al. | |
| 2008/0276866 A1 | 11/2008 | Madriaga et al. | |
| 2008/0305242 A1 | 12/2008 | Wen et al. | |
| 2009/0035449 A1 | 2/2009 | Chen et al. | |

OTHER PUBLICATIONS

U.S. Appl. No. 10/255,913, filed Sep. 26, 2002, Tang et al.

\* cited by examiner

*Primary Examiner* — Dah-Wei Yuan
*Assistant Examiner* — Charles Capozzi
(74) *Attorney, Agent, or Firm* — Squire Sanders (US) LLP

(57) ABSTRACT

A systems and method for reducing coating defects on a stent may involve a support apparatus comprising wire cage for carrying a stent. The support apparatus may have no structure that extends inside the stent. A support apparatus may include a plurality of wires that pass through the stent but do not pass through the midplane of the stent. A support apparatus may contact only the proximal ends of the stent. The method may involve keeping the stent in motion during a spray coating process to prevent the stent from having a point remain in continuous contact with a support apparatus.

18 Claims, 7 Drawing Sheets

SYSTEM FOR COATING A STENT

FIELD OF THE INVENTION

Briefly and in general terms, the present invention generally relates to coating a medical device and, more specifically, to a system and method for supporting a stent during a coating process.

BACKGROUND OF THE INVENTION

In percutaneous transluminal coronary angioplasty (PTCA), a balloon catheter is inserted through a brachial or femoral artery, positioned across a coronary artery occlusion, and inflated to compress the atherosclerotic plaque to open, by remodeling, the lumen of the coronary artery. The balloon is then deflated and withdrawn. Problems with PTCA include formation of dissections, intimal flaps and torn arterial linings, all of which can create another occlusion in the lumen of the coronary artery. Moreover, thrombosis and restenosis may occur several months after the procedure and create a need for additional angioplasty or a surgical bypass operation. Stents are used to address these issues. Stents are small, intricate, implantable medical devices and are generally implanted to stop negative remodeling, reduce occlusions, inhibit thrombosis and restenosis, and maintain patency within vascular lumens such as, for example, the lumen of a coronary artery.

The treatment of a diseased site or lesion with a stent involves both delivery and deployment of the stent. Stent delivery refers to introducing and transporting the stent through an anatomical lumen to a desired treatment site, such as a lesion in a vessel. An anatomical lumen can be any cavity, duct, of a tubular organ such as a blood vessel, urinary tract, and bile duct. Stent deployment corresponds to expansion of the stent within the anatomical lumen at the region requiring treatment. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen with the stent remaining at the treatment location.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

Stents are often modified to provide drug delivery capabilities to further address thrombosis and restenosis. Stents may be coated with a polymeric carrier impregnated with a drug or therapeutic substance. A conventional method of coating includes applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer.

The size of the treatment region within an anatomical lumen may vary. Multiple stents may be deployed adjacent to each other to treat relatively large regions of a vessel. However, positioning and deployment of multiple stents can be time consuming and may require a specialized delivery device capable of accommodating multiple stents. There are also issues associated with the regions where the stents meet. If the multiple stents are not abutted closely, there can be regions between the stents which are not treated. To avoid this, when serial stents are implanted, they are typically overlapped. Overlapping creates other issues. The overlapped stent regions are stiffer and allow for less natural movement of the vessel. They also have a double thickness of struts which must be endothelialized for complete healing and, in the case of drug eluting stents, they have double the load of drug and carrier polymer. There can be certain economies associated with using a single 2× length stent as apposed to two 1× length stents as the manufacturing cost of producing a 2× length stent is not twice the cost of producing two 1× length stents. For these many reasons, longer stents may be used, such as stents with an overall length greater than 30 mm. However, methods and devices for coating shorter stents may produce a greater incidence of coating defects in longer stents. Coating defects may include non-uniform surface characteristics, non-uniform thickness, bare spots, and flaking. FIGS. 13 and 14 show coating defects on the luminal or inner surface of a stent having a 4 mm overall diameter and 38 mm overall length. It is desirable to minimize coating defects for several reasons. Coating defects can serve as an initiation site for coating peeling or flaking that can create embolic debris. The rough surface generated, and stagnant regions of blood flow in the case of flaps or packets can serve as a nidus for thrombus formation. Furthermore, coating defects can lead to undue variation in the amount, concentration, and release rate of the drug from the stent coating.

Accordingly there is a continuing need for a coating method and system that minimizes stent coating defects, especially for longer stents.

SUMMARY OF THE INVENTION

Briefly and in general terms, the present invention is directed to a system for coating a stent.

In some aspects of the present invention, a system comprises a stent having a central axis that extends from a distal end of the stent to a proximal end of the stent; an apparatus that supports the stent, wherein the apparatus comprises a container carrying the stent and a device that rotates the container, and the container is configured to prevent the stent from rotating on an axis perpendicular to the central axis of the stent; and a coating device adjacent to the apparatus, the coating device configured to discharge a coating substance onto the stent, wherein the container has no point that remains in continuous contact with the stent while the container rotates 360 degrees.

In some aspects of the present invention, a system comprises a stent having a central axis that extends from a distal end of the stent to a proximal end of the stent; an apparatus that supports the stent, wherein the apparatus comprises a container carrying the stent and a device that rotates the container, and the container is configured to prevent the stent from rotating on an axis perpendicular to the central axis of the stent; and a coating device adjacent to the apparatus, the coating device configured to discharge a coating substance onto the stent, wherein the apparatus rotates the stent about the central axis of the stent, and the apparatus has no point that remains in continuous contact with the stent while the stent rotates 360 degrees.

The features and advantages of the invention will be more readily understood from the following detailed description which should be read in conjunction with the accompanying drawings.

DETAILED DESCRIPTION OF THE PREFERRED EMBODIMENTS

Figure 1:
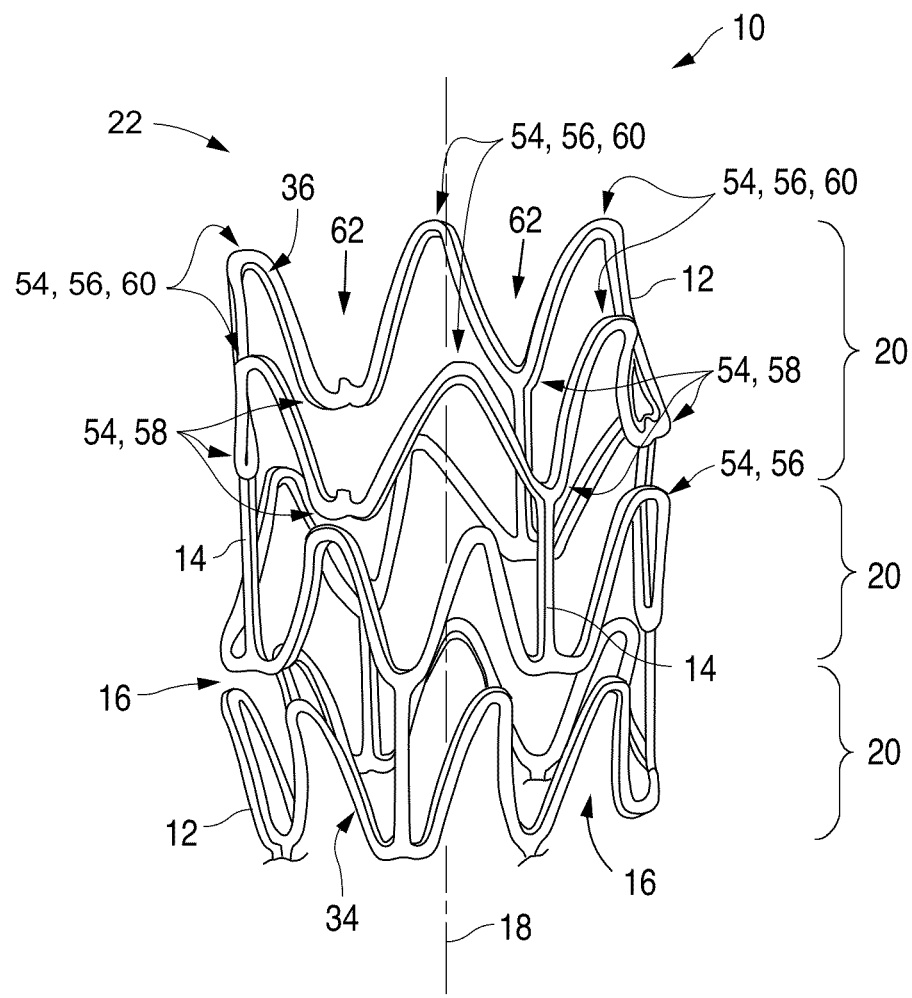
FIG. 1 is a partial perspective view of a stent showing a stacked set of ring structures forming a portion of an overall tubular structure.

Referring now in more detail to the exemplary drawings for purposes of illustrating embodiments of the invention, wherein like reference numerals designate corresponding or like elements among the several views, there is shown in FIG. 1 a stent 10 having an overall body shape that is hollow and tubular. FIG. 1 shows a proximal portion of the stent 10. In some embodiments, the stent can be made from wires, fibers, coiled sheet, with or without gaps, or a scaffolding network of rings. The stent can have any particular geometrical configuration, such as a sinusoidal or serpentine strut configuration, and should not be limited to what is illustrated in FIG. 1. The variation in stent patterns is virtually unlimited. The stent can be balloon expandable or self-expandable, both of which are well known in the art. The stent is preferably for cardiovascular use. In other embodiments, the stent can be used in another anatomical lumen, including without limitation peripheral vasculature.

Figure 2:
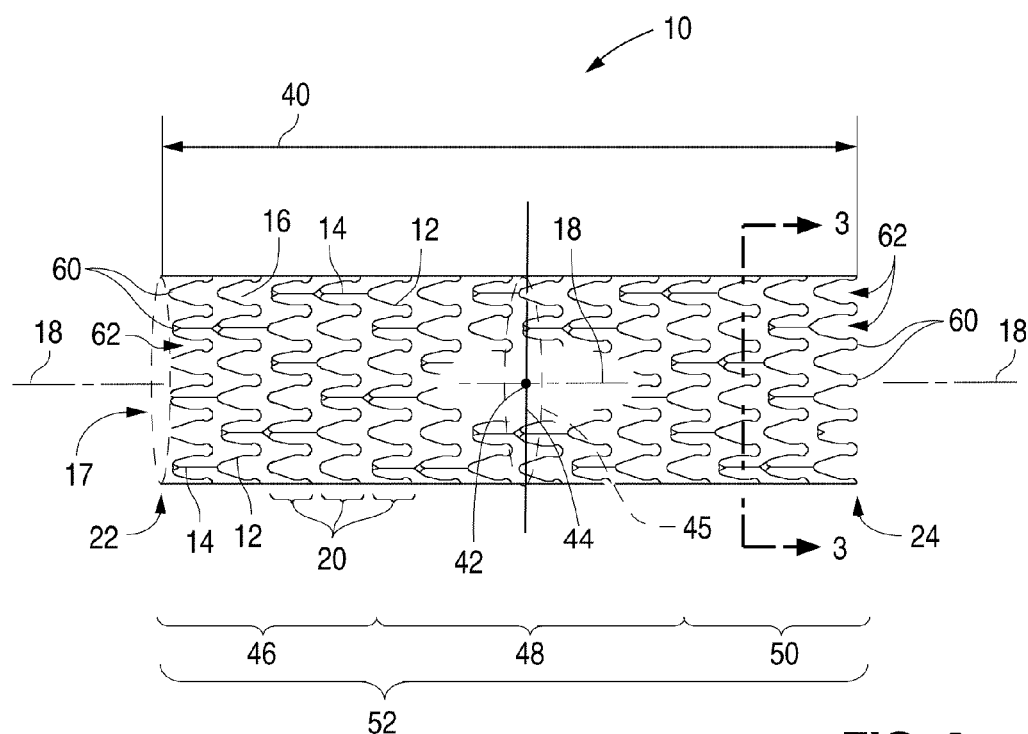
FIG. 2 is a simplified view of an entire stent showing an overall tubular structure formed by a distal segment, a middle segment, proximal segment.

FIGS. 1 and 2 show stents with two different stent patterns. The stents are illustrated in an uncrimped or expanded state. In both FIGS. 1 and 2, the stent 10 includes many interconnecting struts 12, 14 separated from each other by gaps 16. The struts 12, 14 can be made of any suitable material, such as a biocompatible metal or polymer. In FIG. 2, the stent 10 has an overall body 52 having a tube shape with a central passageway 17 passing through the entire longitudinal length of the stent. The central passageway has two circular openings, there being one circular opening at each of the distal and proximal ends 22, 24 of the overall tubular body 52. A central axis 18 runs through the central passageway in the center of the tubular body. At least some of the struts 12 are arranged in series to form sinusoidal or serpentine ring structures 20 that encircle the central axis 18. The ring structures 20 are arranged serially along the central axis 18 to form the overall tubular body 52 of the stent 10. Each ring structure 20 is connected to an immediately adjacent ring structure 20 by interconnecting struts 14. One ring 20 is located at the distal end 22 of the stent 10, and another ring 20 is located at the opposite, proximal end 24 of the stent.

Figure 3:
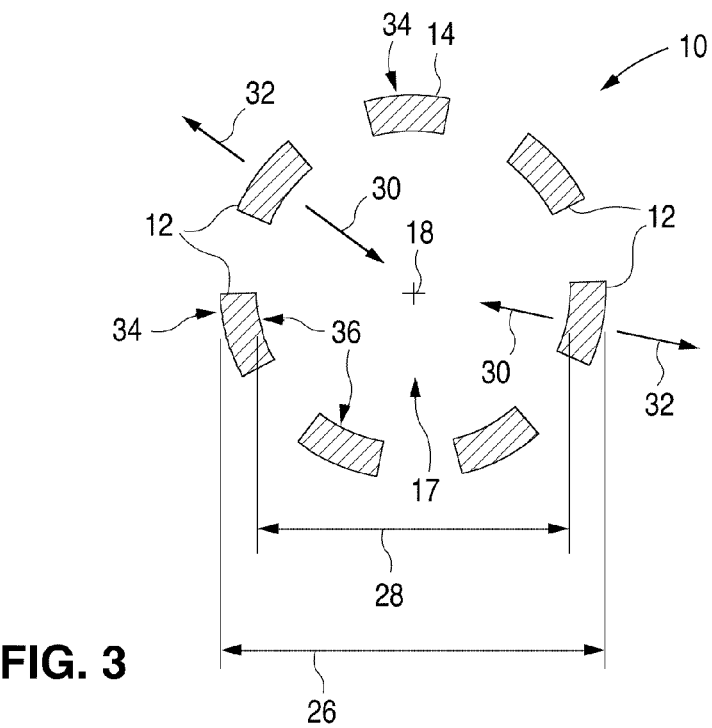
FIG. 3 is a cross-sectional view along line 3-3 of FIG. 2, showing inward and outward facing surfaces of the stent.

FIG. 3 is an exemplary cross-sectional view of the stent 10 along line 3-3 in FIG. 2. There can be any number of struts 12, 14 along line 3-3, which runs perpendicular to the central axis 18 of the stent 10. In FIG. 3, the cross-section of seven struts 12, 14 are shown for ease of illustration.

As shown in FIG. 3, the struts 12, 14 in cross-section are arranged in a circular pattern having an outer diameter 26 and an inner diameter 28. The circular pattern encircles the central axis 18. A portion of the surface of each strut faces radially inward in a direction 30 facing toward the central axis 18. A portion of the surface of each strut faces radially outward in a direction 32 facing away from the central axis 18. The various stent surfaces that face radially outward collectively form the outer surface 34 of the stent 10. The various stent surfaces that face radially inward collectively form the inner surface 36 of the stent 10.

The terms "axial" and "longitudinal" are used interchangeably and relate to a direction, line or orientation that is parallel or substantially parallel to the central axis of a stent or a central axis of a cylindrical structure. The term "circumferential" relates to the direction along a circumference of a stent or a circular structure. The terms "radial" and "radially" relate to a direction, line or orientation that is perpendicular or substantially perpendicular to the central axis of a stent or a central axis of a cylindrical structure. For example, in FIG. 3, arrows 30, 32 point in opposite radial directions and the outer and inner diameters 26, 28 can be measured along radial directions.

Referring again to FIG. 2, the stent 10 has an overall length 40 that is measured axially from the distal end 22 to the proximal end 24, along the entire tubular body 52 of the stent. The stent 10 also has an axial midpoint 42 within the central passageway 17. The axial midpoint 42 is shown through a partial cutaway of the overall tubular body of the stent 10. The axial midpoint 42 is located on the central axis 18 and halfway between the distal and proximal ends 22, 24 of the stent 10. The axial midpoint 42 is surrounded by the struts 12, 14 and may be encircled by one of the ring structures 20. A radial midline 44 intersects the central axis 18 at the axial midpoint 42.

A midplane 45 runs through and contains the axial midpoint 42 and the radial midline 44. The midplane 45 is bounded by the outer surface 34 of the stent and is located half way between the distal and proximal ends 22, 24 of the stent 10. That is, the midplane 45 does not extend beyond the outer surface 34 of the stent 10. The outer surface 34 defines, or at least forms part of, the outer boundary of the midplane 45. The midline 44 and midplane 45 are perpendicular to the central axis 18.

The stent 10 also has a distal segment 46, a middle segment 48, and a proximal segment 50. The distal segment 46 starts at the distal end 22 and extends toward the proximal end 24. The proximal segment 50 starts at the proximal end 24 and extends toward the distal end 22. The middle segment 48 contains the axial midpoint 42 and is located between the distal and proximal segments 46, 50. Together the distal, middle, and proximal segments 46, 48, 50 form the overall tubular body of the stent 10.

Referring again FIGS. 1 and 2, the struts 12 of each ring structure 20 are arranged end to end, forming a sinusoidal or undulating pattern. In the illustrated embodiments, the undulating pattern of each ring structure 20 includes a series of V- or W-like shapes arranged circumferentially. The ends of the struts 12 are connected by bending elements 54 (FIG. 1) which are configured to bend and flex during crimping, stent delivery, and stent deployment. The bending elements 54 allow elongate portions of the struts 12, which are relatively straight, to move in relation to each other, thereby allowing the elongate portions to collapse toward one another during crimping and to spread apart during stent deployment.

As shown in FIG. 1, the undulating pattern of each ring structure 20 includes an alternating series of peaks 56 and valleys 58 at the bending elements 54 (elements 56, 58 and 54 are not in FIG. 2, but are in FIG. 1. Should this first sentence refer to FIG. 1?). The peaks 56 and the valleys 58 are high points and low points, respectively, on each ring structure 20. At the distal and proximal ends 22, 24 of the stent 10, crowns 60 protrude out in axial directions and form the circumferential edges of the overall tubular body 52 of the stent 10. The crowns can be either peaks 56 or valleys 58. The crowns 60 at the proximal end 24 (FIG. 2) form the proximal edge of the stent 10. The crowns 60 at the distal end 22 (FIGS. 1 and 2) form the distal edge of the stent 10. The crowns 60 are spaced apart from each other by circumferential gaps 62 bounded in part by elongate portions of the struts 12 and bending elements 54.

Figure 4:
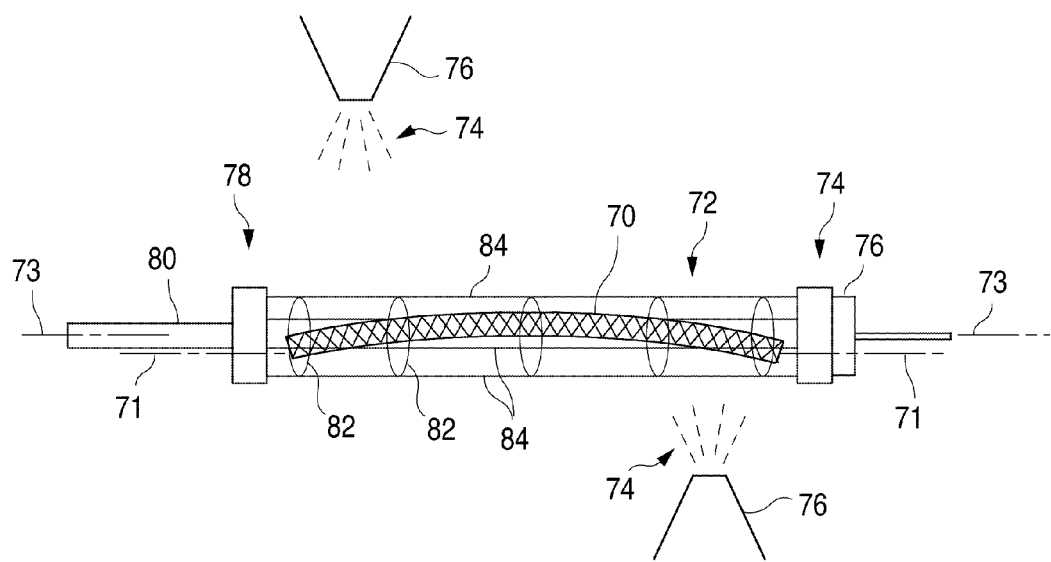
FIG. 4 is a perspective view of a support apparatus having no structure inside the central passageway of a stent, showing the stent enclosed within a wire cage positioned adjacent nozzles for applying a coating substance onto the stent.

FIG. 4 shows a stent 70 with a slight curvature over its overall length. The stent 70 can be over 30 mm in overall length. The curvature may be an intentional aspect of the stent design or may be the result of a manufacturing variation. Manufacturing variations that may cause curvature could include handling of the stent during secondary processes, such as descaling and electropolishing of metal stent struts, weighing processes, or manipulation of the stent between the various manufacturing steps. The stent central axis 71 is a straight line that passes through the respective center point of each circular opening of the stent central passageway at the distal and proximal ends of the stent.

The stent 70 is placed in and enclosed within a small cylindrical cage 72. The stent 70 will move about or rattle within the cage 72 as the cage is rotated about its longitudinal axis 73. The stent 70 may move about due to rotation of the cage and/or under the action of a spray plume 74 of coating substance projected out of one or more nozzles 76 located at a distance away from the cage, or from the action of gas directed from a drying nozzle. The nozzles 76 are configured to discharge a coating substance using any device including but not limited to an air pressure source, an external air assisted atomizer, an internal air assisted atomizer, a piezoelectric transducer, and an electrostatic device.

In some embodiments, the cage is not rotated and the stent moves about solely due to the spray plume 74 which applies a rotational force on the stent 70. The nozzles 76 may be moved relative to the cage so as to cause a change in direction of the force applied by the spray plume on the stent 70 that keeps the stent constantly moving. Also, the cage can be moved relative to the nozzle so as to cause a change in direction of the force applied by the spray plume on the stent 70 that keeps the stent constantly moving. The relative movement can be rotational, linear, or a combination of both.

The stent 70 is supported by the cage 72, so there can be one or more contact points between the stent and cage at any time. Movement of the stent 70 within the cage 72, whether due to cage rotation, the spray plume or other cause, assures that there are no permanent contact points between the cage and stent. That is, a particular point of contact between the stent 70 and the cage 72 exists only momentarily before the stent shifts in relation to the cage and forms a different point of contact. The periodic or continuous movement of the stent allows all portions of the stent to be coated over a period of time. Also, it believed that constant movement reduces or prevents the occurrence of coating defects due to pooling or webbing of the coating substance at contact points. The inner diameter of the cage is sized large enough so that stents with a maximum degree of bend can still rattle around inside the cage by at least a small amount.

With continued reference to FIG. 4, at the distal end 74 of the cage 72 there is a removable cap 76. Removal of the cap 76 from the cage 72 allows a stent to be placed inside and removed from the cage 72. At the proximal end 78 of the cage 72 there is a connection member 80 that may be engaged to an electric motor or other machine that rotates or linearly translates the cage 72.

The cage 72 includes circumferential wires 82 and longitudinal wires 84 that support and retain the stent 70. Any wire pattern may be used. The illustrated embodiment includes five circumferential wires 82 and four longitudinal wires 84, although any number of wires 82, 84 may be used as appropriate for the size of the stent 70. In some embodiments, the circumferential wires 82 are inside the longitudinal wires 84 to minimize the size of the temporary contact points between the stent 70 and the cage 72.

The cage wires 82, 84 form, at least in part, the boundary of a holding space for holding the stent 70. In some embodiments, the number of cage wires 82, 84 are minimized so that there is just enough to support and retain the stent 70. The number of wires may depend on the size and shape of the stent. For example, there can be only one longitudinal wire 84 with two or more circumferential wires 82. In a further example, there can be only three longitudinal wires 84 with no circumferential wires. Minimizing the number of cage wires will also minimize shadowing or masking of the stent 70 by the wires. Shadowing and masking refers to the condition where one or more of the cage wires covers a portion of the stent 70 so that the portion receives less coating substance than other portions of the stent. Inducing the stent 70 to continuously move or rattle inside the cage 72 during all or part of the coating process will also allow portions of the stent that were masked by the cage wires to be adequately coated at a later time during the coating process. Any diminishment of the spray flux by the cage wires is expected to be averaged out due to movement of the stent 70 relative to the cage 72 and/or nozzles 76.

In some embodiments, contact points between the stent 70 and one or more of the cage wires 82, 84 lasts no longer than the time for rotating the cage by a predetermined angle of rotation about the cage longitudinal axis 73. The predetermined angle of rotation can be 720 degrees (two revolutions), more narrowly 360 degrees (one revolution), and more narrowly 180 degrees (half a revolution), and more narrowly 90 degrees (quarter revolution). In some embodiments, the cage wires are configured so that they have no point that remains in continuous contact with the stent 70 while the cage axially rotates 720 degrees, more narrowly 360 degrees, and more narrowly 180 degrees, and more narrowly 90 degrees.

In some embodiments, the cage 72 is a substantially open structure, in that the cage allows the spray plume to enter the cage and allows any sprayed substance that does not contact the stent to pass through the other side of the cage with minimal obstruction. In this manner, accumulation of the coating substance inside the cage is minimized or prevented altogether.

In some embodiments, the stent 70 is forced to rotate about the stent central axis 71. In some embodiments, the cage 72 prevents the stent 70 from rotating on an axis perpendicular to the stent central axis 71 during the spray coating process. In some embodiments, the cage 72 keeps the stent oriented so that the stent central axis 71 remains parallel or substantially parallel to the cage longitudinal axis 73. In some embodiments, the cage 72 is sized to allow only one stent to fit inside the cage. In some embodiments, the cage 72 is sized to prevent the stent 70 from moving out from the path of the spray plume 74. That is, the cage elements 82, 84 prevent the stent 70 from being forced from the spray area directly in front of the nozzles 76. In some embodiments, the nozzles 76 are oriented tangentially to the outer surface of the stent.

It will be appreciated that the cage of FIG. 4 includes no part that extends into the central passageway of the stent 70. Also, all points of contact between the sent 70 and the cage 72 are only on the stent outer surface. The cage wires can be made of any material, including but not limited to metal, polymer, natural fiber, or combinations thereof. The cage wires can be a flexible string, fiber or filament that is pulled in tension.

Figure 5:
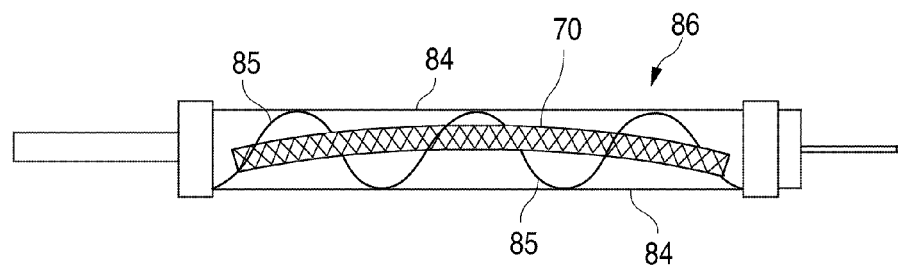
FIG. 5 is a perspective view of a support apparatus having no structure inside the central passageway of a stent, showing the stent and a helical wire that spirals around the stent.

FIG. 5 shows a cage 86 with elements similar to the cage 72 of FIG. 4 except that the cage 86 includes a helical wire 85 that spirals around the stent 70. The helical wire 85 defines, at least in part, a holding space in which the stent 70 is located. The helical wire 85 defines, at least in part, the boundary of the holding space. As the cage 86 is rotated, portions of the helical wire 85 that were masking the stent 70 from the spray plume 74 will move out of the way to allow the stent to be coated more uniformly. It is also believed that rotation of the helical wire about the cage central axis 73 will keep points of contact between the stent and the cage continuously changing. In some embodiments, the cage 86 includes multiple coiled wires forming the boundary of a holding space for the stent. In some embodiments, the cage 86 has no longitudinal wires that form a boundary for the holding space.

Figure 6:
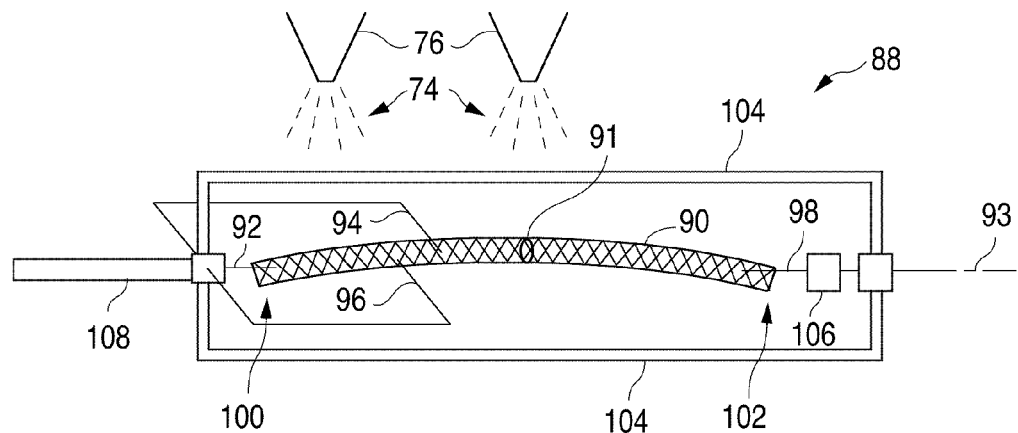
FIG. 6 is a perspective view of a support apparatus having no structure passing through the midplane of the stent, showing the stent retained by a plurality of wires including end wires that support the end of the stent and transverse wires that rotationally engage the stent.

Referring next to FIG. 6, the ends of a stent 90 are supported on thin wires 92, 98 of a support apparatus 88. A middle segment of the stent 90 is rotated by other wires 94, 96. The wires 92, 94, 96, 98 extend a small distance into the stent central passageway, though none of the wires pass through the stent midplane 91. Longitudinal end wires 92, 98 extend partially into the proximal end 100 and distal end 102 of the stent. The end wires 92, 98 enter the stent central passageway through the circular openings formed by ring structures at the proximal and distal ends 100, 102, as opposed to entering through gaps between stent struts. The end wires 92, 98 are located only at the end segments of the stent tubular body and do not pass through the middle segment of the stent tubular body. In some embodiments, the end wires 92, 98 extend into the stent tubular body by no more than 40% of the overall length of the stent, more narrowly no more than 25% of the overall length of the stent, more narrowly no more than 10% of the overall length, and more narrowly no more than 5% of the overall length.

The end wires 92, 98 are parallel or substantially parallel to the central axis 93 of the stent 90. The end wires 92, 98 do not transmit any significant rotational torque to the stent 90. The end wires 92, 98 by themselves are incapable of rotating the stent 90 about the stent central axis 93. The end wires 92, 98 may be journaled or coupled to the support apparatus 88 in such a way to allow the end wires 92, 98 to axially rotate or spin freely and independently of other parts of the support apparatus. In another embodiment, the end wires 92, 98 only rotate if the support apparatus 88 is rotated.

The end wires 92, 98 are held in position by support members 104 that run the entire overall length of the stent 90. A release device 106 attached to one of the end wires 98 is configured to allow the end wire to be retracted or slid out of the stent 90 so as to allow removal of the stent and installation of another stent. The release device 106 may include a knob for user manipulation and a spring that biases or urges the end wire 98 into the stent.

Transverse wires 94, 96 transmit torque or rotational force to the stent 90. The illustrated embodiment shows two transverse wires 94, 96, though any number of transverse wires 94, 96 may be used to rotate the stent 90. The transverse wires 94, 96 pass through gaps between stent struts. The transverse wires 94, 96 extend at a ninety-degree angle or other non-zero angle relative to the central axis of the stent 90. The transverse wires 94, 96 are connected to a connection member 108 at a second end of the support apparatus 88. The connection member 108 is configured to transmit torque or rotational force from an electric motor to the transverse wires 94, 96. Activating the motor causes axial rotation of the connection member 108, which causes rotation of the transverse wires 94, 96, which cause rotation of the stent 90. In some embodiments, the transverse wires 94, 96 may connect to support members 104.

The transverse wires 94, 96 may be sufficiently flexible to allow a user to pull the tips of the wires 94, 96 out of the stent 90 to allow removal of the stent and installation of another stent. In some embodiments, the transverse wires 94, 96 enter a segment of the overall stent body that does not contain the end wires 92, 98.

As the stent 90 with the support apparatus 88, the stent will shift around slightly and, thus, avoid any permanent contact points between the stent and the support wires 92, 94, 96, 98. That is, contact points between the stent 70 and the support apparatus 88 exist temporarily during the coating process. In some embodiments, contact points between the stent and one or more of the wires 92, 94, 96, 98 lasts no longer than the time for rotating the stent by a predetermined rotational angle about the stent central axis. The predetermined angle can be 720 degrees, more narrowly 360 degrees, and more narrowly 180 degrees. In some embodiments, the wires 92, 94, 96, 98 are arranged and configured so that they have no point that remains in continuous contact with the stent 90 while the stent rotates 720 degrees about the stent central axis, more narrowly 360 degrees, and more narrowly 180 degrees.

With continued reference to FIG. 6, in some embodiments the stent 90 may be rotated under the action of a spray plumes 74 of coating substance projected out of one or more spray nozzles 76 located at a distance away from the support apparatus 88. In some embodiments, there are no transverse wires and the stent 90 is allowed to rotate freely and independently of the support apparatus 88. In some embodiments, stent 90 is induced to move solely due to the spray plume 74 applying a rotational force on the stent. The nozzles 76 may be oriented so as to direct the spray plume 74 tangentially to the stent outer surface. The nozzles 76 and the support apparatus 88 may be moved relative to each other so as to cause a change in direction of the force applied by the spray plume on the stent 90 that keeps the stent constantly moving.

Figure 7:
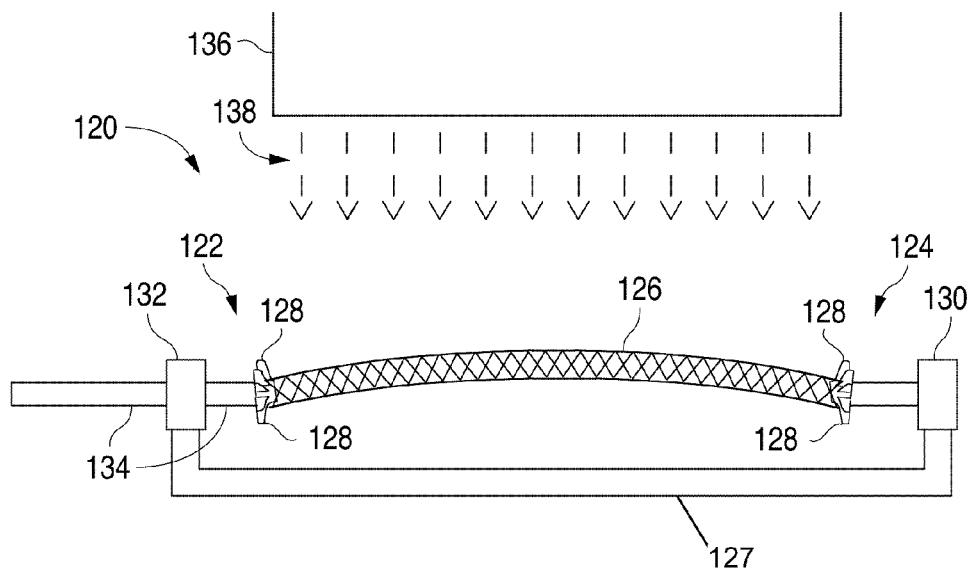
FIG. 7 is a perspective view of a support apparatus having no structure contacting a stent except at distal and proximal ends of the stent, showing the stent supported by a plurality of engaging elements configured to mate with the ring structure at the distal and proximal ends of the stent.

Referring next to FIG. 7, a support apparatus 120 includes two support devices 122, 124 at opposite ends of a stent 126. The support devices 122, 124 are connected to each other by a base member 127 that spans longitudinally across the entire overall length of the stent. The support devices 122, 124 include protruding elements 128 that project radially outward away from each other. The protruding elements 128 are sized and shaped to interdigitate with the ring structures at the proximal and distal ends of the stent.

In some embodiments, the protruding elements 128 are shaped to mate with the undulating ring structures at the proximal and distal ends. The protruding elements 128 fit into the circumferential gaps separating the crowns of the ring structures at the proximal and distal ends. The protruding elements 128 extend partially into the stent central passageway. When the support devices 122, 124 are rotated, the protruding elements 128 exert torque or a rotational force on elongate portions of the stent struts forming the ring structures. When rotated, the protruding elements 128 push the stent struts in a circumferential direction.

In some embodiments, the support devices 122, 124 include a biasing device, such as a spring or an electric motor, that biases or urges the protruding elements 128 into the circumferential gaps. The biasing devices may also allow the support devices 122, 124 to slide and move apart from each other to allow removal of the stent 126 and installation of another stent on the support apparatus 120. In a further embodiment, one or both of support devices 122, 124 are slidable with respect to one another to accommodate stents of varying length.

The support devices 122, 124 can include any number of protruding elements 128. For example, each support device 122, 124 can have only one protruding element 128 or only two protruding elements. In some embodiments, the protruding elements 128 push axially against bending elements that interconnect the stent struts. In some embodiments, the protruding elements 128 are arranged and positioned so as to support the stent 126 loosely, wherein the protruding elements do not press axially against the bending elements or any other part of the stent. In this manner, the stent 126 may shift position on the support devices 122, 124 so that there is no point on the support devices 122, 124 that remains in continuous contact with the stent 90 while the stent rotates 720 degrees about the stent central axis, more narrowly 360 degrees, and more narrowly 180 degrees, and more narrowly 90 degrees.

In some embodiments, one of the support devices 124, is journaled or rotatably coupled on a bearing 130 of the support apparatus 120 in such a way to allow the support device 124 to axially rotate or spin freely and independently of other parts of the support apparatus. In this way, the support device 124 is rendered incapable of applying any torque or rotational force on the stent 126.

In some embodiments, one of the support devices 122 is supported on a bearing 132 and is actively driven by an electric motor or machine engaged on a connection member 134 passing through the bearing 132. In some embodiments, the opposite support device 124 is not actively driven, but is allowed to rotate freely due to rotation of the stent 126.

The base member 127 is positioned opposite a coating applicator 136 configured to project a coating substance toward the stent 126. The stent 126 is located between the coating applicator 136 and the base member 127 to avoid shadowing and masking of the stent 126. The coating applicator 136 may be a spray nozzle or series of spray nozzles.

With continued reference to FIG. 7, in some embodiments the stent 126 may be rotated under the action of a spray plume 138 from the coating applicator 136. In some embodiments, the support devices 122, 124 do not induce rotation of the stent 126 so that the stent is allowed to rotate freely and independently of the support apparatus 120. In some embodiments, the stent 126 is induced to move solely due to the spray plume 138 applying a rotational force on the stent. In some embodiments, the coating applicator 136 is oriented so that the spray plume 138 is concentrated on an off-center or tangential portion of the stent to induce axial rotation of the stent.

It will be appreciated that in FIG. 7 no portion of the support apparatus 120 contacts the stent 126 except at end segments of the stent. In some embodiments, no portion of the support apparatus 120 contacts the stent 126 except at the outermost ring structures at the distal and proximal ends of the stent. In some embodiments, there are no points on the stent 126 that continuously remain in contact with the support apparatus 120 while the stent rotates.

Figure 8:
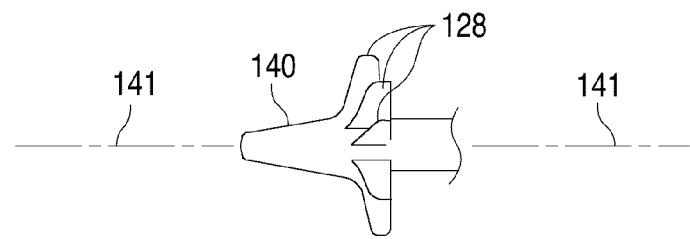
FIG. 8 is a perspective view of radially protruding elements for supporting and/or rotating a stent.

In some embodiments, as shown in FIG. 8, the support devices 122, 124 include a tapered longitudinal element 140. The protruding elements 128 project radially outward from the longitudinal element 140 and an axis of rotation 141 of the support device. The longitudinal element 140 is shaped and configured to enter the central passageway of the stent through the circular openings formed by ring structures at the proximal and distal ends of the stent, as opposed to entering through gaps between stent struts. In some embodiments, the longitudinal element 140 extends into the stent tubular body up to 40% of the overall length of the stent, more narrowly up to 25% of the overall length of the stent, more narrowly up to 10% of the overall length, and more narrowly up to 5% of the overall length. In some embodiments, the longitudinal element 140 is a thin wire. In some embodiments, no part of the support devices 122, 124 extend into the central passageway of the stent beyond the outermost ring structures at the proximal and distal ends of the stent.

Figure 9:
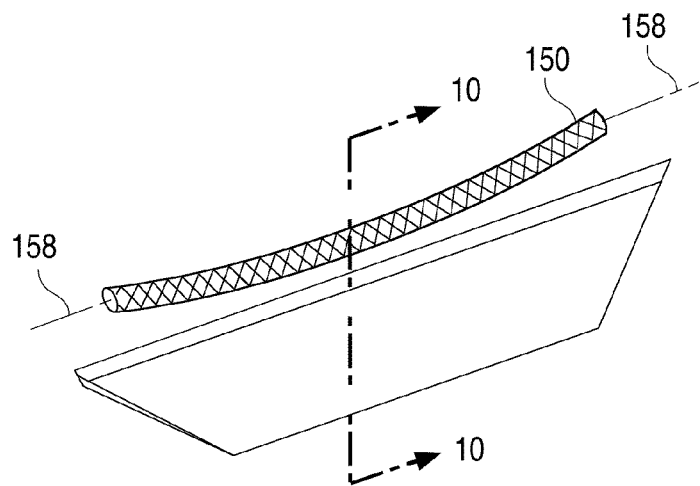
FIG. 9 is a perspective view showing a stent rotated by a tangential stream of air from an air nozzle.
Figure 10:
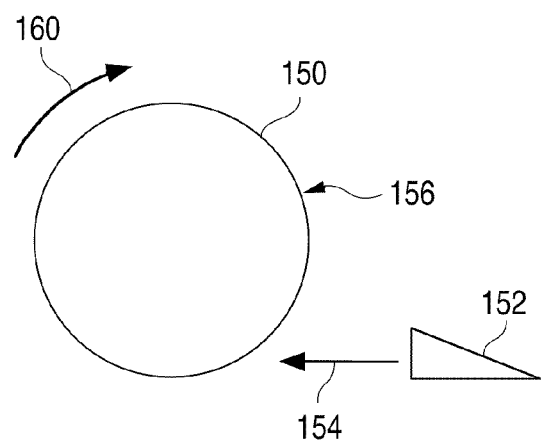
FIG. 10 is a cross-sectional view along line 10-10 in FIG. 9.

Referring now to FIGS. 9 and 10, rotation of a stent 150 can be induced by a focal air flow at a lower or upper edge of the stent. The stent 150 may be supported in any manner that allows axial rotation of the stent, including but not limited to the support structures described in connection with FIGS. 4-8. An air nozzle 152 is configured and positioned to project a focused stream of air in a direction 154 that is substantially tangential to the abluminal or outer surface 156 of the stent 150. The air nozzle 152 is connected to a pressurized air source. All or a majority of the air from the air nozzle 154 is directed below the central axis 158 of the stent 150 so that the stent is induced to rotate about the central axis as indicated by arrow 160. In other embodiments, the air from the air nozzle 154 is concentrated above the central axis 158 or on any one side of the central axis. In some embodiments, the air nozzle 152 is connected to a source providing a coating substance so that the air stream includes the coating substance to be applied on the stent 150. In some embodiments, in addition to the air nozzle 152 which provides for the rotation of stent 150, there is an additional spray nozzle to apply the coating.

Figure 11:
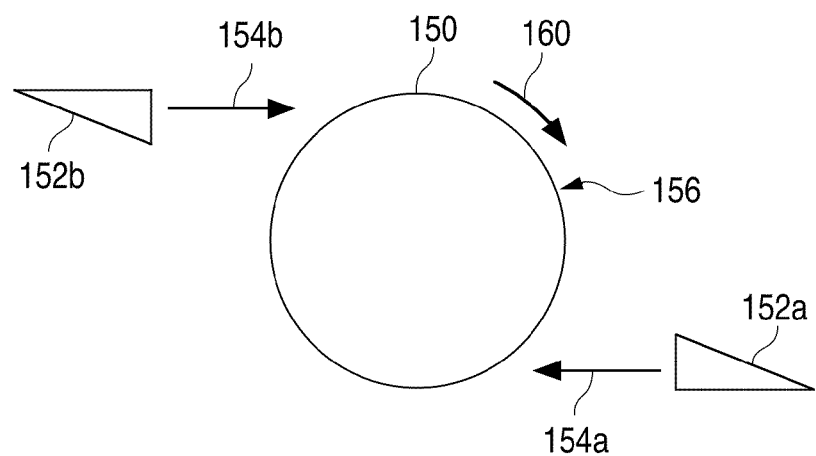
FIG. 11 is a cross-sectional view of a stent rotated by two tangential streams of air from separate air nozzles.

In some embodiments, as shown in FIG. 11, multiple air nozzles 152a, 152b project separate streams of air tangentially on the stent 150. The tangential air streams can be directed at different directions 154a, 154b to different portions of the stent that are off-center from the central axis of the stent.

Figure 12:
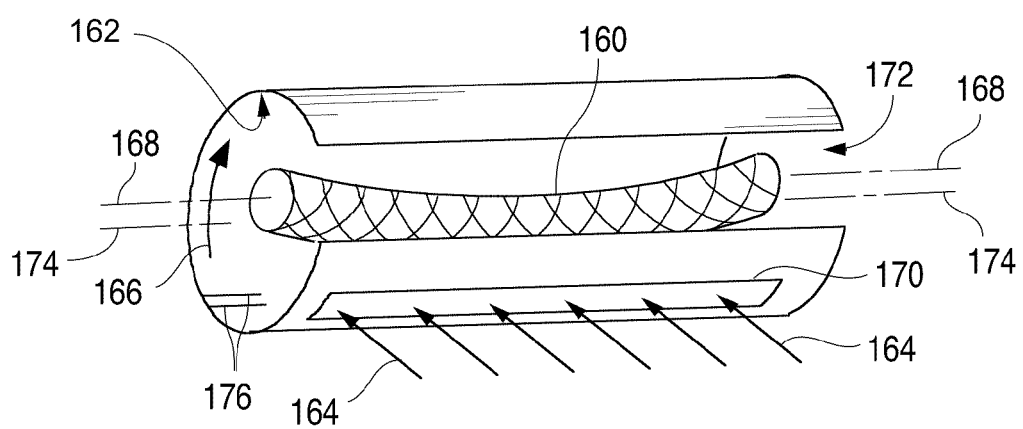
FIG. 12 is a perspective top view of a stent rotated by a stream of air circulated around the stent by a cylindrical surface.
Figure 13:
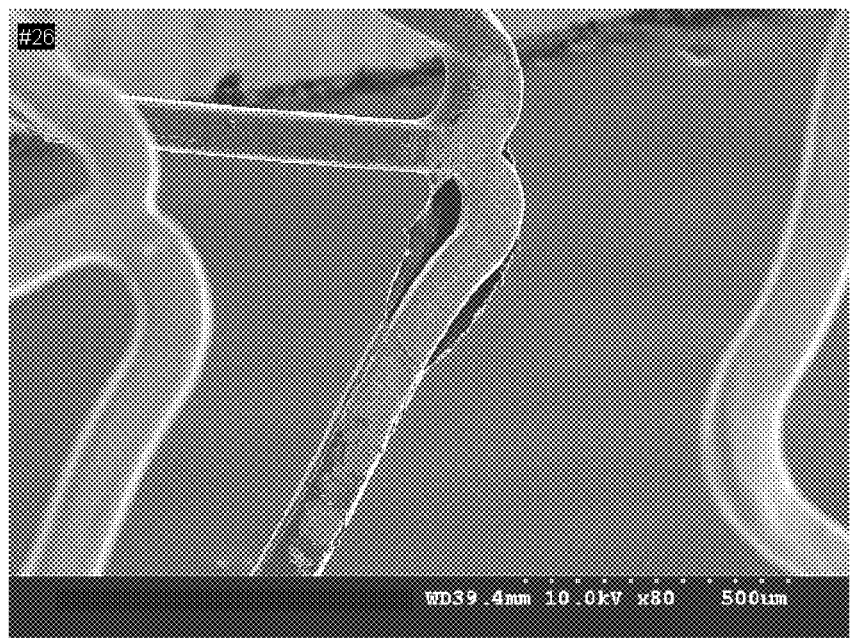
FIGS. 13 and 14 are photographs of stent portions, showing coating defects on the inner surface of the stent.
Figure 14:

FIG. 12 shows a top perspective view of a stent 160 at least partially surrounded by a curved, cylindrical surface 162. The cylindrical surface 162 extends longitudinally along the entire overall length of the stent 160. The cylindrical surface 162 forms a space into which a stream of air 164 is directed. The surface 162 is shaped to channel or direct the stream of air 164 in a circular direction 166 around the outer surface of the stent 160 so that the stent is induced to axially rotate about the stent central axis 168 in the same circular direction 166. The cylindrical surface 162 may have a longitudinal inlet slot opening 170 into which the stream of air is directed. The cylindrical surface 162 may also have a longitudinal outlet opening 172 out of which air may escape after having been circulated around the outer surface of the stent 160.

In operation, the air stream 164 circulates around the stent 160, which keeps the stent constantly moving relative to the surrounding surface 162 while the stent is coated with a coating substance. While the stent moves or rattles, no part of the stent remains in continuous contact with a support structure. The air stream 164 may include a coating substance that coats the stent 160. In some embodiments a coating substance is applied to the stent 160 separately from the air stream 164.

In FIG. 12, the stent 160 may be supported in any manner that allows axial rotation of the stent, including but not limited to the support structures described in connection with FIGS. 4-8. In some embodiments, the stent is supported and retained solely by the cylindrical surface 162. In some embodiments, the cylindrical surface 162 keeps the stent 160 oriented so that the stent central axis 168 remains parallel or substantially parallel to the central axis 174 of the cylindrical surface 162. In some embodiments, the cylindrical surface 162 has a plurality a circular cross-sections, the surface central axis 174 passes through the center point of each of the circular cross-section, and the stent central axis 168 and the surface central axis 174 are parallel or substantially parallel to each other. In some embodiments, the cylindrical surface 162 includes a plurality of straight lines 176 that are parallel or substantially parallel to each other and to the stent central axis 168. In some embodiments, the cylindrical surface 162 is sized to prevent the stent 160 from moving out from the path of the air stream 164.

In the above described embodiments, the stent can be sized for any anatomical lumen. In some embodiments, the stent has an outer diameter of 3 mm. In some embodiments the stent is 33 mm in overall length. In other embodiments, the stent is 38 mm in overall length. In some embodiments, the stent is over 38 mm in overall length.

In the above embodiments, the coating substance may include a polymeric carrier impregnated with a drug or therapeutic substance. The polymeric carrier may be a polymer dissolved in a solvent, and the drug dispersed in the blend. Examples of drugs that can be coated on stents using the method of the present invention include any moiety capable of contributing to a therapeutic effect, a prophylactic effect, both a therapeutic and prophylactic effect, or other biologically active effect in a mammal. An agent can also be coated which has a diagnostic property. The drug or bioactive agents include, but are not limited to, small molecules, nucleotides, oligonucleotides, polynucleotides, amino acids, oligopeptides, polypeptides, and proteins. In one example, the drug or bioactive agent inhibits the activity of vascular smooth muscle cells. In another example, the drug or bioactive agent controls migration or proliferation of smooth muscle cells to prevent or inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. For example one end of a stent can be supported by one end wire shown in FIG. 6 while the opposite end of the stent can be supported with the protruding elements shown in FIG. 8. Accordingly, it is not intended that the invention be limited, except as by the appended claims.

What is claimed is:

1. A system for coating a stent, the system comprising:
a stent having a central axis that extends from a distal end of the stent to a proximal end of the stent;
an apparatus that supports the stent, wherein the apparatus comprises a container carrying the stent and a device that rotates the container, and the container is configured to prevent the stent from rotating on an axis perpendicular to the central axis of the stent; and
a coating device adjacent to the apparatus, the coating device configured to discharge a coating substance onto the stent,
wherein the container has no point that remains in continuous contact with the stent while the container rotates 360 degrees.

2. A system for coating a stent, the system comprising:
a stent having a central axis that extends from a distal end of the stent to a proximal end of the stent;
an apparatus that supports the stent, wherein the apparatus comprises a container carrying the stent and a device that rotates the container, and the container is configured to prevent the stent from rotating on an axis perpendicular to the central axis of the stent; and
a coating device adjacent to the apparatus, the coating device configured to discharge a coating substance onto the stent,
wherein the apparatus rotates the stent about the central axis of the stent, and the apparatus has no point that remains in continuous contact with the stent while the stent rotates 360 degrees.

3. The system of claim 1, wherein a stream of gas rotates the stent and the stream of gas is discharged from a blower adjacent the stent or from the coating device.

4. The system of claim 3, wherein the blower is configured to concentrate the stream of gas onto a portion of the stent that is off-center from the central axis of the stent.

5. The system of claim 3, further comprising a curved surface that faces toward the outer surface of the stent, the curved surface shaped to circulate the stream of gas in a circular direction around the outer surface of the stent to induce rotation of the stent around the central axis of the stent.

6. The system of claim 1, wherein the container includes a wire forming a boundary of a holding space within the container, the holding space sized to receive the stent.

7. The system of claim 6, wherein the wire is one of a plurality of straight wires of the container, each one of the wires extending along the entire overall length of the holding space.

8. The system of claim 6, wherein the wire is one of a plurality of curved wires of the container, each one of the wires encircling the holding space.

9. The system of claim 6, wherein the wire spirals around the holding space.

10. The system of claim 6, wherein the holding space is sized to receive only one stent within the holding space.

11. The system of claim 1, wherein the container is sized to allow only one stent to fit inside the container.

12. The system of claim 1, wherein when the coating substance is discharged from the coating device, the container prevents the stent from moving out of the path of the coating substance.

13. The system of claim 2, wherein the container includes a wire forming a boundary of a holding space within the container, the holding space sized to receive the stent.

14. The system of claim 13, wherein the wire is one of a plurality of straight wires of the container, each one of the wires extending along the entire overall length of the holding space.

15. The system of claim 13, wherein the wire is one of a plurality of curved wires of the container, each one of the wires encircling the holding space.

16. The system of claim 13, wherein the wire spirals around the holding space.

17. The system of claim 13, wherein the holding space is sized to receive only one stent within the holding space.

18. The system of claim 2, wherein the container is sized to allow only one stent to fit inside the container.

* * * * *